(12) United States Patent
Li et al.

(10) Patent No.: US 9,248,443 B2
(45) Date of Patent: Feb. 2, 2016

(54) SULFUR-CONTAINING PALLADIUM-CARBON CATALYST AND METHOD FOR PREPARING AND USING THE SAME

(75) Inventors: Xiaonian Li, Hangzhou (CN); Qunfeng Zhang, Hangzhou (CN); Xinmin Chen, Shanghai (CN); Feng Feng, Hangzhou (CN); Lei Ma, Hangzhou (CN); Chunshan Lu, Hangzhou (CN); Chunsheng Li, Shanghai (CN)

(73) Assignee: Jiangsu Sinorgchem Technology Co., Ltd., Taizhou, Jiangsu Province (CN)

( * ) Notice: Subject to any disclaimer, the term of this patent is extended or adjusted under 35 U.S.C. 154(b) by 0 days.

(21) Appl. No.: 13/549,384

(22) Filed: Jul. 13, 2012

(65) Prior Publication Data

US 2013/0079559 A1 Mar. 28, 2013

(30) Foreign Application Priority Data

Sep. 22, 2011 (CN) .......................... 2011 1 0284001

(51) Int. Cl.
| | |
|---|---|
| *B01J 37/20* | (2006.01) |
| *C07C 209/26* | (2006.01) |
| *B01J 23/44* | (2006.01) |
| *B01J 27/045* | (2006.01) |
| *B01J 31/22* | (2006.01) |
| *B01J 37/03* | (2006.01) |
| *B01J 21/18* | (2006.01) |

(52) U.S. Cl.
CPC ............ *B01J 37/20* (2013.01); *B01J 23/44* (2013.01); *B01J 27/045* (2013.01); *B01J 31/226* (2013.01); *C07C 209/26* (2013.01); *B01J 21/18* (2013.01); *B01J 37/035* (2013.01); *B01J 2231/32* (2013.01); *B01J 2531/824* (2013.01)

(58) Field of Classification Search
None
See application file for complete search history.

(56) References Cited

U.S. PATENT DOCUMENTS 4,210,602 A * 7/1980 Bergfeld et al. ............... 564/398
4,404,401 A * 9/1983 Zengel et al. .................. 564/416

FOREIGN PATENT DOCUMENTS

| CN | 200610161327.2 | | 6/2008 | |
| CN | 101733169 | * | 6/2010 | ............ C07C 209/26 |

OTHER PUBLICATIONS

Chaston et al. Platinum Metals Rev., 1961, 5, (4), 122-125.*
"Palladium on Activated Carbon Catalyst," National Standard of the P.R. China, GB/T 23518-2009, Promulgated by the General Administration of Quality Supervision, Inspection, and Quarantine of the P.R. China and Standardization Administration of the P.R. China, promulgated on Apr. 8, 2009 and effective on Feb. 1, 2010.

* cited by examiner

*Primary Examiner* — Clinton Brooks
(74) *Attorney, Agent, or Firm* — Manni Li; Mei & Mark LLP

(57) ABSTRACT

A sulfur-containing palladium-carbon catalyst prepared by loading palladium on an active carbon, mixing the palladium-carbon catalyst with a solvent to form a slurry, adding a sulfide to the slurry to treat the loaded palladium under a predetermined temperature, and removing liquid and drying to obtain the catalyst. The sulfur-containing palladium-carbon catalyst is suitable for making phenylene diamine rubber antioxidant with improved productivity and selectivity.

31 Claims, 1 Drawing Sheet

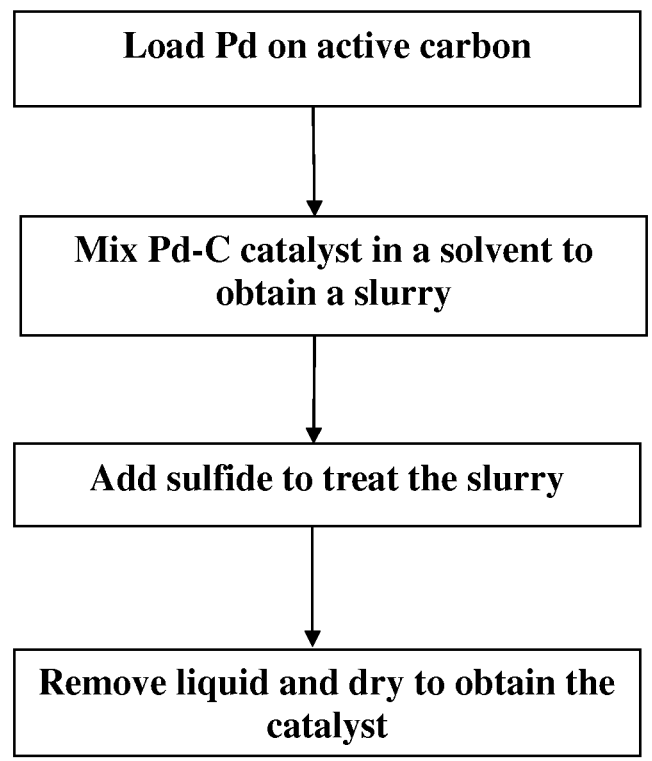

SULFUR-CONTAINING PALLADIUM-CARBON CATALYST AND METHOD FOR PREPARING AND USING THE SAME

CROSS-REFERENCE AND RELATED APPLICATION

The subject application claims priority on Chinese patent application No. 201110284001.X filed on Sep. 22, 2011. The contents and subject matter of the Chinese priority application is incorporated herein by reference.

TECHNICAL FIELD OF THE INVENTION

The present invention relates to catalyst for making p-phenylenediamines, particularly, a sulfur-containing palladium-active carbon catalyst and method for preparing the catalyst and using the catalyst for making p-phenylenediamines.

BACKGROUND OF THE INVENTION

Para-phenylenediamines (PPDs) are known as rubber antioxidants with good performance and widely used in the industry. PPDs are produced by various methods, among which the commonly used are the reductive alkylation method, the phenol-amine condensation method, the hydroxylamine reductive alkylation method, and the quinonimine condensation method. Reductive alkylation of 4-aminodiphenylamine (4-ADPA) and an aliphatic ketone is one of the most important synthetic methods currently used in the industry. For example, N-(1,3-dimethylbutyl)-N'-phenyl-para-phenylenediamine (6PPD) is an important anti-degradant for rubbers and functions as an antiozonant, antioxidant, thermoresisting reagent, and flex cracking resisting reagent for rubbers. 6PPD has been widely used as the popularity of the meridian tire arises. 6PPD may be prepared by hydrogenation dehydration of 4-ADPA and methylisobutyl ketone (MIBK) in the presence of a catalyst in a one-step process as follows:

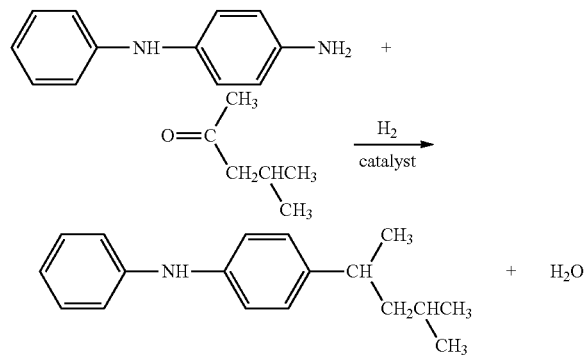

The reductive alkylation may also be a two-step process, during which 4-ADPA and MIBK react through dehydration condensation to form an imine, and the imine is subsequently reduced by hydrogen to 6PPD:

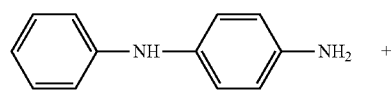

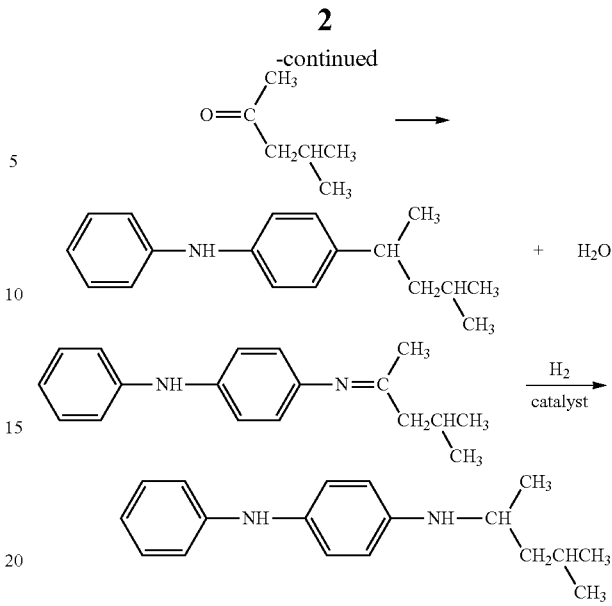

The first step of the reaction may be conducted in the presence of a proton acid catalyst or without a catalyst. The second step must be carried out in the presence of a hydrogenation catalyst with good selectivity.

In the hydrogenation reductive alkylation for preparing the PPD rubber antioxidant, major side reactions include hydrogenation of the raw materials to form the corresponding alcohols, hydrogenolysis of the raw materials or products, hydrogenation of the benzene ring, and tar generated by overheating, etc. The key to obtaining PPD rubber anti-degradants with good quality and low cost is to use a catalyst with good activity and selectivity, and can be recycled and reused.

Currently, catalysts for making PPD rubber antioxidants in the industry include copper-based catalyst and the platinum-carbon catalyst. Chinese Patent No. 200610161327.2 discloses a method for preparing a Cu—Zn/Al$_2$O$_3$ catalyst for the reductive alkylation for making 6PPD. The copper-based catalyst costs less, however, the selectivity is not optimal. In the presence of the copper-based catalyst, a large amount of MIBK is hydrogenated and reduced to the corresponding alcohol (MIBA), and the percentage of MIBA at the end of the reaction can reach between 9.3 to 97.4% of the total amount of the MIBK and MIBA. As a result, the raw material is wasted, and the cost is increased. On the other hand, the metal platinum in the conventional platinum-carbon catalyst is very expensive, and the production cost is greatly increased by the bulk use of the catalyst during the industrial production.

Palladium (Pd) has been commonly used as a hydrogenation catalyst in the hydrogenation reduction of the nitro group, carbonyl group, carbon double bond, and carbon-to-nitrogen double bond. However, when palladium-carbon containing catalyst is used as the hydrogenation catalyst in the reductive alkylation for making 6PPD, the raw material and the product have side reactions of hydrogenolysis of their respective C—N bonds so that the selectivity for 6PPD is very low.

To this date, palladium has not been successfully used as an active component in the catalyst for making PPD rubber antioxidants with high conversion rate and high selectivity, because it is still difficult to control the side reactions of C—N bond hydrogenolysis caused by palladium-containing catalysts.

SUMMARY OF THE INVENTION

The present invention provides a sulfur-containing palladium-carbon catalyst and method for preparing and using the same. The catalyst of the present invention exhibits high selectivity in comparison with the copper-based catalyst and avoids the high cost of the platinum-carbon catalyst.

The sulfur-containing palladium-carbon catalyst of the present invention may be prepared as follows: loading palladium on an active carbon to obtain a palladium-carbon catalyst; mixing the palladium-carbon catalyst with a solvent to obtain a slurry; adding a sulfide into the slurry and stifling under a predetermined temperature to treat the slurry; and removing liquid from the sulfide-treated slurry and drying to obtain the sulfur-containing palladium-carbon catalyst.

Preferably, the molar ratio of the sulfide added in the slurry for the treatment to the palladium loaded on the palladium-carbon catalyst is in the range of about 0.1:1 to 10:1. More preferably, the molar ratio of the added sulfide to the loaded palladium is in the range of about 0.1:1 to 1:1.

Preferably, the sulfide used in the present invention may be a thiol, thioether, alkyl disulfide, thiofuran, hydrogen sulfide, ammonium sulfide, ammonium hydrosulfide, sulfide of an alkaline metal, hydrosulfide of an alkaline metal, or a mixture thereof.

More preferably, the sulfide may be methyl mercaptan, ethyl thiol, methyl thioether, ethyl thioether, diphenyl thioether, dimethyl disulfide, thiofuran, hydrogen sulfide, ammonium sulfide, ammonium hydrosulfide, sodium sulfide, and potassium hydrosulfide, or a mixture thereof. Most preferably, the sulfide is diphenyl thioether or dimethyl disulfide.

In the method of the present invention, the solvent for making the slurry with the palladium-loaded active carbon catalyst may be any alcohols, ketones, or water, such as methanol, ethanol, acetone, methyl isobutyl ketone, isopropanol, tert-butanol, isoamyl ketone, octanone, water, or a mixture thereof.

In the method of the present invention, the granularity of the active carbon may be about 50 to 1-000 meshes. The specific surface area of the active carbon is about 600 to 1800 $m^2/g$. The loading amount of palladium on the active carbon in the catalyst is about 0.5 to 10 wt % of the total weight of the catalyst.

The present invention further provides a sulfur-containing palladium-carbon catalyst prepared by the method. The present invention further provides a sulfur-containing palladium-carbon catalyst that comprises an active carbon and a sulfide-treated palladium loaded on the active carbon. In the catalyst of the present invention, the loaded palladium is about 0.5 to 10 wt % of the catalyst, and the loaded palladium is partially passivated by the sulfide at the molar ratio of the sulfide used for treatment to the loaded palladium of about 0.1:1 to 10:1.

The present invention further provides a method for making PPD rubber antioxidants. In the method, 4-ADPA and an aliphatic ketone are used as the starting material, and the sulfur-containing palladium-carbon catalyst of the present invention is used as the catalyst, to make the PPDs. Preferably, the sulfur-containing palladium-carbon catalyst is added into the reaction system in an amount such that the weight ratio of the loaded palladium on the catalyst to the 4-ADPA is about 0.01 to 1 wt %.

Preferably, the method for producing PPD has the following steps: using the 4-ADPA and an aliphatic ketone as the starting material, adding the sulfur-containing palladium carbon catalyst directly into the reaction system while stirring, flowing a predetermined amount of hydrogen into the reaction system, and producing the PPD through liquid phase hydrogenation. Alternatively, the method for producing PPD has the following steps: reacting 4-ADPA and an aliphatic ketone, while keeping stirring, in the presence of a protonic acid or an active carbon as the catalyst at a temperature of about 120° C. to 150° C. to form an intermediate (an imine or a Schiff base) via dehydration condensation, adding the sulfur-containing palladium carbon catalyst into the reaction system having the intermediate and a solvent, flowing a predetermined amount of hydrogen into the reaction system, and forming the PPDs via liquid phase hydrogenation.

The sulfur-containing palladium-carbon catalyst prepared in accordance with the present invention exhibits good activity, selectivity, and reusability, and may be used for producing the PPD rubber antioxidants. The catalyst of the present invention improves not only the yield of the PPD rubber antioxidant but also the selectivity of the reaction by reducing the reduction of the starting material to the corresponding alcohol and eliminating the hydrolysis of the C—N bonds in the raw material and the products.

BRIEF DESCRIPTION OF THE DRAWINGS

FIG. 1 is a flow chart showing the steps of preparing the sulfur-containing palladium-carbon catalyst in the present invention.

DETAILED DESCRIPTION OF THE INVENTION AND EMBODIMENTS

As shown in FIG. 1, the sulfur-containing palladium-carbon catalyst of the present invention is prepared as follows: loading palladium on an active carbon to obtain a palladium-carbon catalyst; mixing the palladium-carbon catalyst with a solvent to obtain a slurry; adding a sulfide to the slurry and treating the slurry with the sulfide by stirring thoroughly under a predetermined temperature; and removing liquid from the treated slurry and drying to obtain the sulfur-containing palladium-carbon catalyst.

In the present invention, Pd is initially loaded onto the active carbon, and then reacts with the sulfide while loaded on the active carbon so as to be passivated. As a result, the use of the catalyst reduces the side products produced during the production of the PPD rubber antioxidants. It is unexpected to discover that the Pd loaded on the active carbon can not be completely converted to palladium sulfide by the sulfide, and the sulfur is selectively adsorbed and combined on the surface of the palladium particles to form various forms of palladium sulfides. Because of the selective adsorption of the sulfur onto the Pd and various Pd sulfides formed in existence, the activity of the Pd carried on the active carbon is passivated, and thus, the C—N bond hydrogenolysis side reactions in the raw materials and products are greatly reduced. Subsequently, the selectivity of the reaction is improved.

The content of sulfur in the palladium-carbon catalyst of the present invention after being treated with the sulfide may vary, depending on the type and amount of the sulfurizing reagent, used for the treatment. The general trend is that the more the sulfurizing reagent is used, the more sulfide adsorbed or combined or both on the palladium-carbon catalyst. However, the amount of sulfide that is on the catalyst is not always proportional to the amount of the sulfide used for the treatment. Moreover, when different sulfides are used to treat the palladium-carbon catalyst, the amount of sulfide that is on the catalyst after the treatment may vary. As long as the sulfurization process is conducted under the conditions and the sulfurizing reagent is used as provided in the present invention, the catalyst of the present invention may be obtained.

In the present invention, the step of loading the palladium on the active carbon may be carried out in accordance with the conventional loading procedure known to one of ordinary skill in the art. For example, the palladium-carbon catalyst may be prepared as follows: an active carbon used for preparing the catalyst is weighed and stirred in a solvent to form a slurry at the temperature of about 60° C. to 90° C. The solvent used to form the slurry may be water or any other solvent known to one of ordinary skill in the art. Palladium in the form of $H_2PdCl_4$ solution is slowly added dropwise into the slurry while stirring thoroughly. After an immersion of about 0.5 to 5 hours, the pH value of the solution is adjusted to about 7.1 to 9, and the temperature of the slurry is reduced to room temperature. Then, the slurry is filtered, and the filter cake is washed with deionized water until neutral. Then, the filter cake is dissolved in a solvent to form a slurry at a temperature of about 20° C.-90° C., and a reduction reagent in the liquid form is added dropwise into the slurry. After the reduction reaction is completed, the palladium-carbon catalyst is obtained. The reduction reagent in the reduction step may be formaldehyde, methanol, formic acid, or an alkali metal salt of the formic acid or hydrazine hydrate. Preferably, during the reduction reaction, the molar ratio of the reduction reagent to the palladium is about 2:1 to 200:1, preferably about 5:1 to 50:1. Preferably, the temperature for the reduction reaction is about 20° C. to 100° C., and more preferably, about 30° C. to 80° C. When the reduction reaction is conducted under the preferred conditions, the reaction is more complete and most of the palladium ions loaded on the active carbon are reduced to palladium. The reduction reaction may be conducted during the preparation of the catalyst well in advance or immediately before proceeding to the next step in the method for making the catalyst of the present invention.

In the present invention, preferably, the loading amount of palladium on the catalyst may be controlled to be within a range of about 0.5 to 10 wt %, and preferably about 1 to 5 wt %. The loading amount of the palladium on the catalyst affects the subsequent reactions in that, if the loading amount of the palladium is too low, longer time is required for the reaction for making PPD rubber antioxidants, which is not suitable for industrial production; if the loading amount of the palladium is too high, the stereoselectivity of the product is affected. Nevertheless, the sulfur-containing palladium-carbon catalyst of the present invention, even though the loading amount of palladium is not within the range, may still function well in improving the yield and selectivity of the PPD rubber antioxidants and preventing the raw materials from being reduced to the corresponding alcohols.

The amount of the loaded palladium can normally be precisely determined, and the method for determining the loading amount of the palladium on the catalyst is well known in the art. For example, the National Standard of the P.R. China, GB/T 23518-2009, entitled "Palladium on Activated Carbon Catalyst," provides a standard method for determining the amount of palladium in the palladium-carbon catalyst. The document is incorporated herein by reference.

Preferably, the granularity of the active carbon used in the catalyst of the present invention is about 50 to 1-000 meshes, and more preferably about 80-500 meshes, the specific surface area is about 600 to 1800 $m^2/g$, and preferably about 1000 to 1500 $m^2/g$. At the ranges for the granularity and the specific surface area, the loading of the palladium on the active carbon is easier, and the distribution of the palladium is relatively uniform.

After the palladium-carbon catalyst is obtained, the next step is to mix the palladium loaded active carbon catalyst with a solvent to form a slurry. In the step, the goal is to make the palladium-carbon catalyst into the slurry. Preferably, the solvent has certain polarity so as to optimize the dispersion of the palladium-carbon catalyst therein. The solvent may be any alcohols, ketones, or water. For examples, methanol, ethanol, acetone, methyl isobutyl ketone, isopropanol, tert-butanol, isoamyl ketone, octanone, water, or a mixture thereof may be used. The solvent that can be used in the present invention varies, and there is no stringent requirement for the specific solvent. The solvent may be inexpensive, thus suitable for industrial production.

In addition, during the step of mixing the palladium-carbon catalyst with the solvent to form the slurry, preferably, the volume ratio of the palladium-carbon catalyst to the solvent is controlled at a range of about 1:5 to 1:1000, and more preferably 1:10 to 1:400. If the volume of the solvent is too small, it is difficult to form the slurry; if the volume of the solvent is too big, energy is wasted and post-treatment of the solvent causes problems.

The essential step for preparing the sulfur-containing palladium-carbon catalyst of the present invention is the sulfurizing step. In the step, a sulfide is added to the slurry, and the mixture is stirred thoroughly at a predetermined temperature. During the step, the sulfide and the palladium loaded on the palladium-carbon catalyst thoroughly react so that a portion of the loaded palladium is passivated by the sulfide, and thus, the risk of palladium acting on the C—N bonds in the raw materials or products to cause cracking of the bonds and formation of numerous side products is reduced. Preferably, the molar ratio of the added sulfide and the palladium loaded on the palladium-carbon catalyst is about 0.1:1 to 10:1, and more preferably, 0.1:1 to 1:1. Within the preferred range, the palladium-loaded active carbon catalyst, after the sulfurization, exhibits good catalytic activity, and the hydrogenolysis side reaction can be well controlled. As shown in the examples, however, the Pd loaded active carbon catalyst exhibits certain degree of controllability on the hydrogenolysis side reaction even out of the preferred ranges.

The sulfide in the present invention refers to a sulfurizing reagent that reacts with palladium to have adsorption and coordinating effects so as to reduce the catalytic activity of the palladium. The sulfur atom in the sulfurizing reagent must have lone pair electrons so that it may have the coordinating effect on the palladium. Therefore, the sulfurizing reagent used in the present invention can be any sulfides so long as they have sulfur atoms that have lone pair electrons. Preferably, the sulfide is one or more of thiol, thioether, alkyldisulfide, thiofuran, hydrogen sulfide, ammonium sulfide, ammonium hydrosulfide, sulfide of an alkaline metal, or hydrosulfide of an alkaline metal. More preferably, the sulfide is one or more of methyl mercaptan, ethyl-thiol, methyl-thioether, ethyl-thioether, diphenyl-thioether, dimethyl-disulfide, thiofuran, hydrogen sulfide, ammonium sulfide, ammonium hydrosulfide, sodium sulfide, and potassium hydrosulfide. In the detailed embodiments of the present invention, when the sulfide is diphenyl thioether or dimethyl disulfide, the performance is superior to that of the others.

The predetermined temperature in the sulfurizing reaction process may be about 20° C. to 100° C., preferably about 30° C. to 70° C. Further, the time for sulfurization must be longer than about 10 minutes, preferably about 2 to 5 hours. Therefore, the reaction of the present invention may be accomplished within a wide range of temperature, and the time for the sulfurizing treatment can be very short (generally accomplished in merely longer than 10 minutes). Therefore, energy consumption may be greatly reduced and production cost may be further reduced by adoption of the method of the present invention.

In the detailed embodiments of the present invention, sulfurizing treatment is conducted as follows: after the reduced palladium-carbon catalyst is filtered, the filter cake is washed by deionized water to neutral and vacuum dried at 60° C. to 110° C. Then, it is ready for sulfur treatment. During the step of the sulfur treatment, the reduced palladium-carbon catalyst and a solvent are first prepared to form a slurry at a temperature of about 20° C. to 100° C., and then, a sulfide is added at a molar ratio of palladium to the sulfide of 1:0.1 to 1:10, and the stirring time is longer than 10 minutes. Then, the step of sulfurization is accomplished.

After the sulfurization step, the mixture is immediately filtered to remove the liquid, and the filter cake is dried to obtain the sulfur-containing palladium-carbon catalyst. The filter cake may also be vacuum dried at a temperature of about 30° C. to 110° C. to completely remove the residual solvent in the catalyst. If the solvent that has been used in the sulfurization process may be introduced in the process for making the PPD antioxidants, then, vacuum drying is not required.

The sulfur-containing palladium-carbon catalyst of the present invention is useful for preparing PPD rubber antioxidants. The catalyst of the present invention is suitable for the reaction for preparing PPD antioxidant through the reduction alkylation method. For examples, the catalyst may be used for preparing N-(1,3-dimethyl-butyl)-N'-phenyl para-phenylene diamine (6PPD), N-isopropyl-N'-phenyl para-phenylene diamine (IPPD), N-(1,4-dimethyl pentyl)-N'-phenyl para-phenylene diamine (7PPD), N,N'-di(1,4-imethylpentyl) para-phenylene diamine (77PD), N-sec octyl-N'-phenyl para-phenylene diamine (OPPD), N,N'-di sec-butyl para-phenylene diamine (44PD), N-isoamyl-N'-phenyl para-phenylene diamine (5PPD), N,N'-di(1,3-dimethylbutyl) para-phenylene diamine (66PD), 2,4,6-tri-(N-1,4-dimethylpentyl-para-phenylene diamine)-1,3,5-triazine (TMPPD).

Preferably, the amount of the catalyst added to the reaction is such that the loaded palladium on the catalyst is about 0.01 to 1 wt % of 4-ADPA, and preferably 0.02 to 0.2 wt %. Under the preferable weight percentage, the reaction is complete, and the amount of the catalyst is controlled within the preferred range. Therefore, the production cost is further reduced.

The reduction alkylation method has one-step and two-step procedures. When the catalyst is applied in the one-step procedure, PPD antioxidant is prepared as follows: 4-ADPA and an aliphatic ketone are used as the starting material, the sulfur-containing palladium-carbon catalyst is directly added to the reaction system while stifling, and hydrogen is added into the reaction system at a predetermined amount; the PPD antioxidant is synthesized in the liquid phase hydrogenation.

When the catalyst is applied in the two-step procedure, the PPD antioxidant is prepared as follows: 4-ADPA and an aliphatic ketone are reacted in the presence of a protonic acid or active carbon as the catalyst at a temperature of about 120° C. to 150° C. to form an intermediate after dehydration condensation reaction; the sulfur-containing palladium-carbon catalyst is added to the reaction system containing the intermediate and the solvent, and hydrogen is added into the reaction system at a predetermined amount; the PPD antioxidant is synthesized in the liquid phase hydrogenation.

In the detailed embodiments of the present invention, the catalyst of the present invention may be applied in the preparation of 6PPD. Preferably, the molar ratio of 4-ADPA and MIBK is about 1:2 to 1:10, and more preferably 1:2 to 1:6. Within the range of the molar ratio, the reaction is more complete and suitable for industrial production.

The one-step procedure is as follows: 4-ADPA and methyl isobutyl ketone (MIBK) in excess are used as the starting material, the sulfur-containing palladium-carbon catalyst is added to the reaction system while stifling at a temperature of about 90° C. to 240° C. and hydrogen pressure of about 1 to 5 MPa, and 6PPD is synthesized in the liquid phase hydrogenation. Preferably, in the one-step procedure, the reaction temperature is about 100° C. to 200° C., and the hydrogen pressure is about 1.5 MPa to 3 MPa.

The two-step procedure is as follows: 4-ADPA and methyl isobutyl ketone in excess are used as the starting material and reacted in the presence of a protonic acid or active carbon as the catalyst at a temperature of about 120° C. to 150° C. to form an imine after dehydration condensation reaction; the imine is mixed with methyl isobutyl ketone as the solvent and the sulfur-treated palladium-active carbon catalyst of the present invention as catalyst, at a temperature of about 90° C. to 220° C. and hydrogen pressure of about 1 to 5 MPa; 6PPD is synthesized through the liquid phase hydrogenation reaction. Preferably, in the two-step procedure, the reaction temperature for the dehydration reaction is about 120° C. to 140° C., the reaction temperature for hydrogenation is about 100° C. to 200° C., and the hydrogen pressure is about 1.5 MPa to 3 MPa.

The detailed methods and beneficial results are shown in the following examples, but the scope of the present invention is not limited by the following examples.

Example 1

Active carbon 10 g (at a granularity of 100 meshes, and specific surface area of 1200 $m^2/g$) was added to 100 ml deionized water, and a slurry was prepared at 80° C. 10 ml $H_2PdCl_4$ solution (Pd content is 0.05 g/ml) was slowly added dropwise into the slurry while stirring for 2 hours. 10 wt % NaOH was added to adjust the pH value of the solution to 8, and the temperature of the slurry was reduced to room temperature. The slurry was filtered and the filter cake was washed by deionized water to be neutral; then, the filter cake was prepared to form a slurry at 40° C., and 2 ml 85 wt % hydrazine hydrate solution was added dropwise into the slurry while stifling for 2 hours. The slurry was filtered and the filter cake was washed by deionized water to be neutral, and the filter cake was dried at 100° C. under the vacuum condition. Sulfurization was carried out by mixing the dried filter cake with 100 ml methanol to form a slurry at 40° C., 0.1 ml methyl mercaptan was added dropwise into the slurry while stirring for 2 hours. The slurry was filtered, and the filter cake was dried at 100° C. under the vacuum condition to obtain the sulfur-containing palladium-active carbon catalyst of the present invention.

Example 2

Active carbon 10 g (at a granularity of 200 meshes and specific surface area of 1400 $m^2/g$) was added to 100 ml deionized water, and a slurry was prepared at 60° C. 6 ml $H_2PdCl_4$ solution (content of Pd is 0.05 g/ml) was slowly added dropwise into the slurry while stifling for 3 hours. 10 wt % NaOH was added to adjust the pH of the solution to 8.5, and the temperature of the slurry was reduced to room temperature. The slurry was filtered, and the filter cake was washed by deionized water to neutral. Then, the filter cake was prepared to form a slurry at 60° C., and 10 ml methanol was added dropwise into the slurry while stirring for 4 hours. The slurry was filtered and the filter cake was washed by deionized water to neutral, and the filter cake was dried at 90° C. under the vacuum condition. Sulfurization was carried out, in which the dried filter cake was prepared to form a slurry at 60° C. by mixing in 100 ml alcohol, and 0.1 ml diphenyl thioether was added dropwise into the slurry while stifling for 4 hours. The slurry was filtered, and the filter cake was dried at 80° C. under the vacuum condition to obtain the sulfur-containing palladium-active carbon catalyst of the present invention.

Example 3

Active carbon 10 g (at a granularity of 150 meshes and specific surface area of 1400 m$^2$/g) was added to 100 ml deionized water, and a slurry was prepared at 60° C. 20 ml H$_2$PdCl$_4$ solution (the content of Pd is 0.05 g/ml) was slowly added dropwise into the slurry while stirring for 4 hours. 10 wt % NaOH was added to adjust the pH of the solution to 9, and the temperature of the slurry was reduced to room temperature. The slurry was filtered and the filter cake was washed to be neutral by deionized water. Then, the filter cake was prepared to form a slurry at 60° C., and 35 ml 40 wt % formaldehyde was added dropwise into the slurry while stirring for 4 hours. The slurry was filtered and the filter cake was washed to neutral by deionized water. The filter cake was dried at 90° C. under the vacuum condition. Sulfurization was carried out in which the dried filter cake was prepared to form a slurry at 60° C. by using 200 ml acetone, and 0.8 ml thiofuran was added dropwise into the slurry while stirring for 4 hours. The slurry was filtered and the filter cake was dried at 90° C. under the vacuum condition to obtain the sulfur-containing palladium-active carbon catalyst of the present invention.

Example 4

Active carbon 10 g (at a granularity of 400 meshes and specific surface area of 1600 m$^2$/g) was added to 100 ml deionized water, and a slurry was prepared at 60° C. 4 ml H$_2$PdCl$_4$ solution (the content of Pd is 0.05 g/ml) was slowly added dropwise into the slurry while stirring for 2 hours. 10 wt % NaOH was added to adjust the pH of the solution to be 7.5, and the temperature of the slurry was reduced to room temperature. The slurry was filtered and the filter cake was washed to be neutral by deionized water. Then, the filter cake was prepared to form a slurry at 30° C., and 15 ml 40 wt % formic acid was added dropwise into the slurry while stifling for 4 hours. The slurry was filtered and the filter cake was washed to be neutral by deionized water, and the filter cake was dried at 90° C. under the vacuum condition. Sulfurization was carried out in which the dried filter cake was prepared to form a slurry at 60° C. by using 50 ml methyl isobutyl ketone, and 0.1 ml dimethyl-disulfide was added dropwise into the slurry while stirring for 4 hours. The slurry was filtered, and the filter cake was dried at 110° C. under the vacuum condition to obtain the sulfur-containing palladium-active carbon catalyst of the present invention.

Example 5

Active carbon 10 g (at a granularity of 300 meshes and specific surface area of 1600 m$^2$/g) was added to 100 ml deionized water, and a slurry was prepared at 60° C. 10 ml H$_2$PdCl$_4$ solution (the content of Pd is 0.05 g/ml) was slowly added dropwise into the slurry while stirring for 2 hours. 10 wt % NaOH was added to adjust the pH of the solution to 8.5, and the temperature of the slurry was reduced to room temperature. The slurry was filtered and the filter cake was washed to neutral by deionized water. Then, the filter cake was prepared to form a slurry at 30° C., and 3 ml 85 wt % hydrazine hydrate solution was added dropwise into the slurry while stifling for 4 hours. The slurry was filtered and the filter cake was washed to neutral by deionized water. The filter cake was dried at 90° C. under the vacuum condition. Sulfurization was carried out in which the dried filter cake was prepared to form a slurry at 60° C. by using 200 ml water, and 0.5 ml hydrogen sulfide gas was introduced into the slurry in the form of air bubbles while stifling for 4 hours. The slurry was filtered, and the filter cake was dried at 100° C. under the vacuum condition to obtain a sulfur-containing palladium-active carbon catalyst.

Example 6

Active carbon 10 g (at a granularity of 250 meshes and specific surface area of 1600 m$^2$/g) was added into 100 ml deionized water, and a slurry was prepared at 60° C. 10 ml H$_2$PdCl$_4$ solution (the content of Pd is 0.05 g/ml) was slowly added dropwise into the slurry while stirring for 2 hours. 10 wt % NaOH was added to adjust the pH of the solution to 8.5, and the temperature of the slurry was reduced to room temperature. The slurry was filtered, and the filter cake was washed to neutral by deionized water. Then, the filter cake was prepared to form a slurry at 30° C., and 3 ml 85 wt % hydrazine hydrate solution was added dropwise into the slurry while stifling for 4 hours. The slurry was filtered and a filter cake was washed to neutral by deionized water, and the filter cake was dried at 90° C. under the vacuum condition. Sulfurization was carried out in which the dried filter cake was prepared to form a slurry at 60° C. by using 200 ml water, and 7 ml 10% sodium sulfide at 1.1 g/cm$^3$ was added dropwise into the slurry while stifling for 4 hours. The slurry was filtered, and the filter cake was dried at 110° C. under the vacuum condition to obtain the sulfur-containing palladium-active carbon catalyst of the present invention.

Examples 7 to 13

The preparation steps in Examples 7 to 13 were the same as those of Example 1, except that the active carbon, the loading amount of the palladium, the sulfide, the molar ratio of the sulfide to the palladium, and the solvent used in the slurry were different as shown in Table 1.

Examples 14 to 26

These examples show the application of the catalyst of the present invention.

Example 14

Palladium catalyst 0.74 g as prepared in Example 1, 73.6 g 4-ADPA, and 200 ml MIBK were added to a 500 ml stainless high-pressure reaction kettle. The reaction kettle was closed, and nitrogen was introduced to replace the air inside the reaction kettle for three times, and then hydrogen was introduced to replace the nitrogen for three times. The temperature was increased to 140° C. and the hydrogen pressure was 2 MPa, stirring was started at 900 r/min for 4 hours. The reaction was completed, and the liquid reaction mixture was taken out after the temperature was reduced to room temperature. The liquid reaction mixture was filtered to remove the catalyst, and the filtrate was analyzed by gas chromatography (GC). The results showed that the conversion rate of 4-ADPA was 99.5%, the selectivity of the 6PPD was 99.5%, and the selectivity of the MIBK was 99.8%.

Example 15

Palladium catalyst 0.55 g as prepared in Example 2, 55.2 g 4-ADPA, and 187 ml MIBK were added to a 500 ml stainless high-pressure reaction kettle. The reaction kettle was closed, and nitrogen was introduced to replace the air inside the reaction kettle for three times, and then hydrogen was introduced to replace the nitrogen for three times. The temperature was increased to 160° C. and the hydrogen pressure was 3 MPa. The stirring was started and maintained at 900 r/min for 5 hours. When the reaction was completed, the liquid reaction mixture was taken out after the temperature was reduced to room temperature. The liquid reaction mixture was filtered to remove the catalyst, and the filtrate was analyzed by GC. The results showed that the conversion rate of the 4-ADPA was 99.8%, the selectivity of the 6PPD was 98.7%, and the selectivity of the MIBK was 99.7%.

Example 16

Palladium catalyst 0.74 g as prepared in Example 3, 73.6 g 4-ADPA, and 150 ml MIBK were added to a 500 ml stainless high-pressure reaction kettle. The reaction kettle was closed, and nitrogen was introduced to replace the air inside the reaction kettle for three times, and then hydrogen was introduced to replace the nitrogen for three times. The temperature was increased to 100° C. and the hydrogen pressure was 3 MPa. The stifling was started and maintained at 900 r/min for 3 hours. When the reaction was completed, the liquid reaction mixture was taken out after the temperature was reduced to room temperature. The liquid reaction mixture was filtered to remove the catalyst, and the filtrate was analyzed by GC. The results showed that the conversion rate of the 4-ADPA was 99.3%, the selectivity of the 6PPD was 99.5%, and the selectivity of the MIBK was 99.9%.

Example 17

Palladium catalyst 0.55 g as prepared in Example 4, 55.2 g 4-ADPA, and 225 ml MIBK were added to a 500 ml stainless high-pressure reaction kettle. The reaction kettle was closed, and nitrogen was introduced to replace the air inside the reaction kettle for three times, and then hydrogen was introduced to replace the nitrogen for three times. The temperature was increased to 160° C. and the hydrogen pressure was 1 MPa. The stifling was started and maintained at 900 r/min for 6 hours. When the reaction was completed, the liquid reaction mixture was taken out after the temperature was reduced to room temperature. The liquid reaction mixture was filtered to remove the catalyst, and the filtrate was analyzed by GC. The results showed that the conversion rate of the 4-ADPA was 99.4%, the selectivity of the 6PPD was 99.4%, and the selectivity of the MIBK was 99.6%.

Example 18

Palladium catalyst 1.5 g as prepared in Example 5, 55.2 g 4-ADPA, and 225 ml MIBK were added to a 500 ml stainless high-pressure reaction kettle. The reaction kettle was closed, and nitrogen was introduced to replace the air inside the reaction kettle for three times, and then hydrogen was introduced to replace the nitrogen for three times. The temperature was increased to 220° C. and the hydrogen pressure was 2.5 MPa. The stifling was started and maintained at 900 r/min for 4 hours. When the reaction was completed, the liquid reaction mixture was taken out when the temperature is reduced to room temperature, and the liquid reaction mixture was filtered to remove the catalyst. The filtrate was analyzed by GC. The results showed that the conversion rate of the 4-ADPA was 98.9%, the selectivity of the 6PPD was 99.5%, and the selectivity of the MIBK was 99.2%.

Example 19

4-ADPA 55.2 g, 225 ml MIBK, and 2 g active carbon were added to a 500 ml round bottomed flask with a water segregator. The temperature was raised to 130° C. and the dehydration condensation reaction was conducted for 4 hours while stifling to obtain an imine. Palladium catalyst 0.55 g as prepared in Example 6, the imine, and 150 ml methyl isobutyl ketone were added to a 500 ml stainless high-pressure reaction kettle. The reaction kettle was closed, and nitrogen was introduced to replace the air inside the reaction kettle for three times, and then hydrogen was introduced to replace the nitrogen for three times. The temperature was increased to 200° C. and the hydrogen pressure was 2 MPa. The stifling was started and maintained at 900 r/min for 4 hours. When the reaction was completed, the liquid reaction mixture was taken out after the temperature was reduced to room temperature. The liquid reaction mixture was filtered to remove the catalyst, and the filtrate was analyzed by GC. The results showed that the conversion rate of the 4-ADPA was 99.0%, the selectivity of the 6PPD was 99.6%, and the selectivity of the MIBK was 99.1%.

Examples 20 to 26

The detailed operation steps in Examples 20 to 26 were the same as those of Examples 14 to 19, except that the catalysts and the reaction procedures might vary, which could be one-step or two-step, as shown in Table 2.

Example 27

Preparation of IPPD

Palladium catalyst 0.74 g as prepared in Example 1, 92 g 4-ADPA, and 51 ml acetone were added to a 500 ml stainless high-pressure reaction kettle. The reaction kettle was closed, and nitrogen was introduced to replace the air inside the reaction kettle for three times, and then hydrogen was introduced to replace the nitrogen for three times. The temperature was increased to 150° C. and the hydrogen pressure was 3 MPa. The stifling was started and maintained at 900 r/min for 4 hours. When the reaction was completed, the liquid reaction mixture was taken out after the temperature was reduced to room temperature. The liquid reaction mixture was filtered to remove the catalyst, and the filtrate was analyzed by GC. The results showed that the conversion rate of the 4-ADPA was 99.5%, the selectivity of the IPPD was 99.6%, and the selectivity of the acetone was 99.8%.

Comparative Examples 1 and 2

These comparative examples used untreated palladium-carbon catalysts for catalyzing and synthesizing 6PPD.

Comparative Example 1

Palladium-carbon catalyst 1.5 g 5% (without any sulfurizing treatment), 55.2 g 4-ADPA, and 225 ml MIBK were added to a 500 ml stainless high-pressure reaction kettle. The reaction kettle was closed, and nitrogen was introduced to replace the air inside the reaction kettle for three times, and then hydrogen was introduced to replace the nitrogen for three times. The temperature was increased to 160° C. and the hydrogen pressure was 2.5 MPa. The stifling was started and maintained at 900 r/min for 4 hours. When the reaction was completed, the liquid reaction mixture was taken out after the temperature was reduced to room temperature. The liquid reaction mixture was filtered to remove the catalyst, and the filtrate was analyzed by GC. The results showed that the conversion rate of the 4-ADPA was 99.4%, the selectivity of the 6PPD was 81.6%, and the selectivity of the MIBK was 99.1%.

Comparative Example 2

4-ADPA 55.2 g, 225 ml MIBK, and 2 g active carbon were added to a 500 ml round bottomed flask with a water segregator. The reaction temperature was raised to 130° C. and the dehydration condensation reaction was conducted for 4 hours while stifling to obtain an imine. Palladium-carbon catalyst 0.55 g 3%, the imine, and 150 ml methyl isobutyl ketone were added to a 500 ml stainless high-pressure reaction kettle. The reaction kettle was closed, and nitrogen was introduced to replace the air inside the reaction kettle for three times, and then hydrogen was introduced to replace the nitrogen for three times. The temperature was increased to 180° C. and the hydrogen pressure was 2 MPa. The stirring was started and maintained at 900 r/min for 4 hours. When the reaction was completed, the liquid reaction mixture was taken out after the temperature was reduced to room temperature. The liquid reaction mixture was filtered to remove the catalyst, and the filtrate was analyzed by GC. The results showed that the conversion rate of the 4-ADPA was 99.8%, the selectivity of the 6PPD was 75.2%, and the selectivity of the MIBK was 99.2%.

TABLE 1

Sulfur-Containing Palladium-carbon Catalyst In Examples 1 to 13

| Example | Active Carbon | Loaded Pd (wt %) | Molar Ratio of Sulfide:Pd | Sulfide | Solvent for making the slurry |
|---|---|---|---|---|---|
| 1 | 100 mesh 1200 m$^2$/g | 5 | 0.38:1 | methyl mercaptan | methanol |
| 2 | 200 mesh 1400 m$^2$/g | 3 | 0.21:1 | diphenyl-thioether | ethanol |
| 3 | 150 mesh 1400 m$^2$/g | 10 | 1.05:1 | thiofuran | acetone |
| 4 | 400 mesh 1600 m$^2$/g | 2 | 0.58:1 | dimethyl-disulfide | methyl isobutyl ketone |
| 5 | 300 mesh 1600 m$^2$/g | 5 | — | hydrogen sulfide gas | water |
| 6 | 250 mesh 1600 m$^2$/g | 5 | 2.1:1 | sodium sulfide | water |
| 7 | 50 mesh 600 m$^2$/g | 0.5 | 0.1:1 | ethyl-thiol | ethyl acetate |
| 8 | 1000 mesh 1800 m$^2$/g | 0.3 | 5:1 | ethyl-thioether | ethanol |
| 9 | 1200 mesh 2000 m$^2$/g | 15 | 10:1 | ammonium sulfide | water |
| 10 | 200 mesh 1400 m$^2$/g | 4 | 11:1 | ammonium hydrosulfide | water |
| 11 | 150 mesh 1400 m$^2$/g | 8 | 0.05:1 | potassium hydrosulfide | water |
| 12 | 250 mesh 1600 m$^2$/g | 5 | 4:1 | methyl mercaptan: diphenyl-thioether at 2:1 molar ratio | methanol |
| 13 | 50 mesh 600 m$^2$/g | 0.5 | 8:1 | ammonium sulfide: potassium hydrosulfide at 1:1 molar ratio | water |

TABLE 2

Comparison of the Catalytic Activities

| Example | Catalyst As Prepared in | Reaction Procedure | Amount of the Catalyst(wt %) | Conversion % for 4-ADPA | Selectivity % for 6PPD | Selectivity % of MIBK |
|---|---|---|---|---|---|---|
| 14 | Example 1 | one step | 0.05 | 99.5 | 99.5 | 99.8 |
| 15 | Example 2 | one step | 0.03 | 99.8 | 99.7 | 99.7 |
| 16 | Example 3 | one step | 0.1 | 99.3 | 99.5 | 99.9 |
| 17 | Example 4 | two step | 0.02 | 99.4 | 99.8 | 99.6 |
| 18 | Example 5 | two step | 0.14 | 98.9 | 99.5 | 99.2 |
| 19 | Example 6 | two step | 0.05 | 99.0 | 99.6 | 99.1 |
| 20 | Example 7 | one step | 0.2 | 99.1 | 99.4 | 99.7 |
| 21 | Example 8 | one step | 0.5 | 99.4 | 99.6 | 99.5 |
| 22 | Example 9 | one step | 0.6 | 98.9 | 99.3 | 99.7 |
| 23 | Example 10 | one step | 1.00 | 99.1 | 99.3 | 99.7 |
| 24 | Example 11 | two step | 0.005 | 99.3 | 99.2 | 99.2 |

TABLE 2-continued

Comparison of the Catalytic Activities

| Example | Catalyst As Prepared in | Reaction Procedure | Amount of the Catalyst(wt %) | Conversion % for 4-ADPA | Selectivity % for 6PPD | Selectivity % of MIBK |
|---|---|---|---|---|---|---|
| 25 | Example 12 | two step | 2.00 | 99.3 | 99.4 | 99.8 |
| 26 | Example 13 | two step | 0.8 | 99.5 | 99.2 | 99.8 |
| 27 | Example 1 | one step | 0.05 | 99.5 | 99.6 | 99.8 |
| Comparative Example 1 | untreated Pd/C catalyst | one step | 0.13 | 99.4 | 81.6 | 99.1 |
| Comparative Example 2 | untreated Pd/C catalyst | two step | 0.03 | 99.8 | 75.2 | 99.2 |

As shown in the examples, the catalyst of the present invention exhibited high activity and high selectivity. When the sulfur-containing Palladium-carbon catalyst of the present invention was used in the synthesis of the PPD rubber antioxidants, for example, in the reaction for making 6PPD, the activity and selectivity were high, the conversion rate of the 4-ADPA reached 99.8%, the selectivity of the 6PPD reached 99.5%, and the selectivity of the MIBK was higher than 99.5%. Additionally, the present invention provided low cost for production. The major component of the catalyst of the present invention was palladium, and the loading amount of the palladium was similar to that of the platinum in a platinum-active carbon catalyst. As the palladium-active carbon catalyst was cheaper than the traditional platinum/active carbon catalyst, the economic benefits were higher.

The above embodiments of the present invention do not limit the scope of the present invention. One of ordinary skill in the art may make modifications and variations without departing from the scope of in the invention.

We claim:

1. A sulfur-containing palladium-carbon catalyst, comprising
    active carbon,
    palladium loaded on the active carbon at a loading amount of about 0.5 to 10 wt % of the total weight of the catalyst,
    sulfidized palladium compounds prepared by partially passivating the palladium loaded on the active carbon by a sulfur-containing compound at a molar ratio of the sulfur-containing compound to the palladium of about 0.1:1 to 10:1, and
    the sulfur-containing compound selectively adsorbed on the surface of the catalyst,
    wherein the sulfur-containing compound is selected from the group consisting of a thiol, a thioether, an alkyl disulfide, thiofuran, ammonium hydrosulfide, a hydrosulfide of an alkaline metal, and a mixture thereof.

2. The sulfur-containing palladium-carbon catalyst of claim 1, wherein the active carbon has a granularity of about 50 to 1000 mesh.

3. The sulfur-containing palladium-carbon catalyst of claim 1, wherein the active carbon has a special surface area of about 600 to 1800 m²/g.

4. A sulfur-containing palladium-carbon catalyst as described in claim 1, wherein the catalyst is prepared by
    loading palladium on an active carbon to obtain a palladium-carbon catalyst,
    mixing the palladium-carbon catalyst with a solvent to obtain a slurry,
    adding a sulfur-containing compound to the slurry and treating the palladium-carbon catalyst at a predetermined temperature, and
    removing liquid from the treated palladium carbon catalyst and drying to obtain the sulfur-containing palladium-carbon catalyst.

5. The sulfur-containing palladium-carbon catalyst as described in claim 4, wherein the solvent is methanol, ethanol, acetone, methyl isobutyl ketone, isopropanol, tert-butanol, isoamyl ketone, octanone, water, or a mixture thereof.

6. The sulfur-containing palladium-carbon catalyst as described in claim 1, wherein the sulfur-containing compound is methyl mercaptan, ethyl thiol, methyl thioether, ethyl thioether, diphenyl thioether, dimethyl disulfide, thiofuran, ammonium hydrosulfide, potassium hydrosulfide, or a mixture thereof.

7. A method for preparing a sulfur-containing palladium-carbon catalyst as described in claim 1, comprising
    loading palladium on an active carbon to obtain a palladium-carbon catalyst,
    mixing the palladium-carbon catalyst with a solvent to obtain a slurry,
    adding a sulfide to the slurry and treating the palladium-carbon catalyst at a predetermined temperature, and
    removing liquid from the treated palladium carbon catalyst and drying to obtain the sulfur-containing palladium-carbon catalyst.

8. The method of claim 7, wherein molar ratio of the sulfide added to the slurry to the palladium loaded on the catalyst is about 0.1:1 to 10:1.

9. The method of claim 8, wherein the molar ratio of the sulfide added to the slurry to the palladium loaded on the catalyst is about 0.1:1 to 1:1.

10. The method of claim 7, wherein the solvent is an alcohol, a ketone, water, or a mixture thereof.

11. The method of claim 10, wherein the solvent is methanol, ethanol, acetone, methyl isobutyl ketone, isopropanol, tert-butanol, isoamyl ketone, octanone, water, or a mixture thereof.

12. The method of claim 7, wherein a volume ratio of the palladium-carbon catalyst to the solvent to form the slurry is about 1:5 to 1:1000.

13. The method of claim 7, wherein the active carbon has a granularity of about 50 to 1000 mesh.

14. The method of claim 13, wherein the active carbon has a granularity of about 80 to 500 mesh.

15. The method of claim 7, wherein the active carbon has a special surface area of about 600 to 1800 m²/g.

16. The method of claim 15, wherein the active carbon has the special surface area of about 1000 to 1500 m²/g.

17. The method of claim 7, wherein an amount of palladium that is loaded on the active carbon is about 0.5 to 10 wt % of the total weight of the catalyst.

18. The method of claim 17, wherein the amount of loaded palladium is about 1 to 5 wt % of the total weight of the catalyst.

19. The method of claim 7, wherein the predetermined temperature is about 20° C. to 100° C.

20. The method of claim 7, wherein the palladium loaded on the catalyst is treated with the sulfide for more than 10 minutes.

21. The method of claim 7, wherein the palladium is loaded on the active carbon by
dissolving the active carbon in a first solvent to form a first slurry,
adding a solution containing palladium ions to the first slurry and mixing thoroughly to form a mixture,
adjusting pH of the mixture to about 7.1 to 9 and filtering and washing to obtain a filter cake,
dissolving the filter cake in a second solvent to form a second slurry,
adding a reductive reagent to the second slurry to reduce the palladium ions, and
removing liquid from the reduced second slurry to obtain the palladium-loaded active carbon catalyst.

22. The method of claim 21, wherein the reduction reagent is formaldehyde, methanol, formic acid, or an alkali metal salt of formic acid or hydrazine hydrate.

23. The method of claim 21, wherein a molar ratio of the reduction reagent to the loaded palladium is about 2:1 to 200:1.

24. A method for making para-phenyl diamines comprising reacting 4-ADPA and an aliphatic ketone in liquid phase hydrogenation in presence of the sulfur-containing palladium-carbon catalyst of claim 1.

25. The method of claim 24, wherein an amount of the loaded palladium on the sulfur-containing palladium-carbon catalyst is about 0.01 to 1 wt % of the 4-ADPA.

26. The method of claim 24, wherein the 4-ADPA and the aliphatic ketone are reacted in a one-step procedure.

27. The method of claim 26, wherein the reaction is conducted at about 90° C. to 240° C. and hydrogen gas pressure of about 1 to 5 MPa.

28. The method of claim 24, wherein the 4-ADPA and the aliphatic ketone are reacted in a two-step procedure.

29. The method of claim 28, wherein the 4-ADPA and the aliphatic ketone are reacted to form an intermediate at about 120° C. to 150° C., and the intermediate is reacted with hydrogen gas in a solvent in the presence of the sulfur-containing palladium-carbon catalyst.

30. The method of claim 29, wherein the intermediate is hydrogenated at about 90° C. to 220° C. and hydrogen gas pressure of about 1 to 5 MPa.

31. The method of claim 24, wherein a molar ratio of the 4-ADPA to the aliphatic ketone is about 1:2 to 1:10.

* * * * *